United States Patent [19]

Couillard et al.

[11] Patent Number: 5,755,561
[45] Date of Patent: May 26, 1998

[54] PISTON PUMPING SYSTEM DELIVERING FLUIDS WITH A SUBSTANTIALLY CONSTANT FLOW RATE

[75] Inventors: François Couillard, Noyalo; Dominique Garnier, Orgeval, both of France

[73] Assignees: Francois Couillard, Noyalo; Institute Francais du Petrole, Rueil-Malmaison, both of France

[21] Appl. No.: 548,727

[22] Filed: Oct. 26, 1995

[30] Foreign Application Priority Data

Oct. 26, 1994 [FR] France .................. 94 12936

[51] Int. Cl.$^6$ .................................................. F04B 25/00
[52] U.S. Cl. ........................................ 417/246; 417/248
[58] Field of Search ............................. 417/244, 246, 417/248, 415

[56] References Cited

U.S. PATENT DOCUMENTS

| | | | |
|---|---|---|---|
| 3,704,080 | 11/1972 | Cross | 417/486 |
| 4,311,586 | 1/1982 | Baldwin et al. | 210/101 |
| 4,312,626 | 1/1982 | Juran | 417/244 |
| 4,883,409 | 11/1989 | Strohmeier et al. | 417/43 |
| 5,020,974 | 6/1991 | Searle | 417/246 |
| 5,253,981 | 10/1993 | Yang et al. | 417/3 |
| 5,330,327 | 7/1994 | Anderson | 417/53 |
| 5,538,403 | 7/1996 | Black | 417/453 |

FOREIGN PATENT DOCUMENTS

| | | |
|---|---|---|
| 0303220 | 2/1989 | European Pat. Off. . |
| 0309596 | 4/1989 | European Pat. Off. . |
| 2217020 | 10/1973 | Germany . |
| 2725464 | 12/1978 | Germany . |

Primary Examiner—Timothy Thorpe
Assistant Examiner—Peter G. Korytnyk
Attorney, Agent, or Firm—Antonelli, Terry, Stout, & Kraus, LLP

[57] ABSTRACT

A pumping system in accordance with the invention comprises n ($n \geq 1$) piston or diaphragm primary pumping modules (P1 to Pn) including each at least one pumping unit, connected by means of unidirectional valves (V11–V1n) respectively to n tanks (R1–Rn) containing fluids, a collecting head (CH) receiving the fluids delivered by the various primary modules, and a secondary piston pumping unit (S) for discharging the mixture of fluids collected in this head with a substantially constant flow rate. The pistons are shifted alternately for example by the translation motion of endless screws (9) driven by motors (12). A control set (17-20) associated with position detectors (AC1-ACn) and pressure detectors (C1 to Cn, Cs) proportion the fluids injected and adjust the phases, the piston strokes and their velocities in order to obtain a substantially constant discharge rate. Each primary module can also comprise a second pumping module also allowing a constant rate to be obtained during the suction phase. The invention has application to liquid chromatography.

12 Claims, 7 Drawing Sheets

PISTON PUMPING SYSTEM DELIVERING FLUIDS WITH A SUBSTANTIALLY CONSTANT FLOW RATE

BACKGROUND OF THE INVENTION

1. Field Of The Invention

The present invention relates to a controlled pumping system delivering fluids under pressure with a substantially constant flow rate, usable notably for the injection of fluids into liquid chromatography facilities.

2. Background Of The Invention

Liquid chromatography facilities generally comprise one or several pumps. They draw a "mobile phase" consisting of solvents or mixtures of solvents out of tanks and discharge them into a separation column SC (FIGS. 1, 2) filled with a powdered material called "stationary phase" into which is passed a liquid mixture or sample that is to be separated (analytical chromatography) or purified (preparative chromatography) by means of an injector LS. The flow rates applied can range, as the case may be, from microlitres/minute to greater than ten liters/minute. The pressures prevailing therein can range from 0.1 M.Pascal to greater than ten MPa. In the column, a competition develops for the sample between the stationary phase and the mobile phase. The sample components are more or less retained by the stationary phase according to their molecular structures (the extent of the phenomenon being characterized by a time referred to as retention time) and to the chromatography conditions: type of stationary and mobile phases used, flow rate, etc.

An appropriate detector ES shows the passage of the eluates coming from the column. In analytical chromatography, the information given by the detector provides a quantitative result by the measurement of the areas of the signal peaks detected, and a qualitative result by the measurement of the retention times. In preparative chromatography, the data provided by the detector qualitatively shows an operator the right time for opening the collection valves in order to recover the wanted eluates by means of the collector.

The working principle defined above is that of a chromatograph working in a mode referred to as an "isochratic" mode. It corresponds to the case where the composition of the mobile phase is constant during the complete separation time. There is also another mode, referred to as "elution gradient" mode, which corresponds to more complex cases where it is necessary to vary the composition of the mobile phase during the separation in order to obtain the desired result.

For liquid chromatography operations, one uses either pumping systems called "low pressure" or "upstream gradient" systems, or pumping systems called "high pressure" or "downstream gradient" systems.

Figure 1:
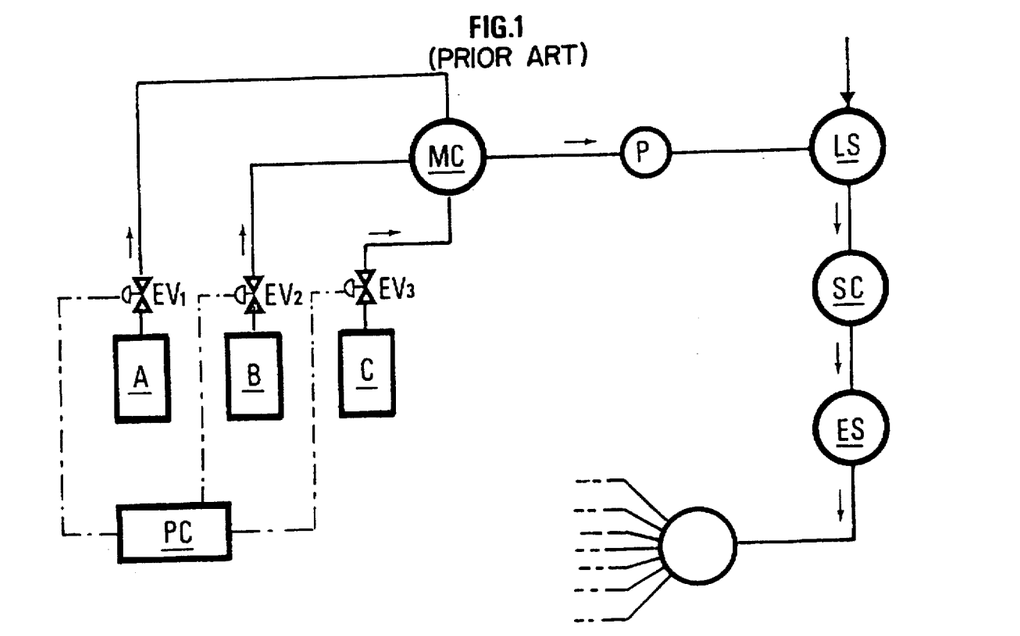
FIG. 1 shows an example of a system of a prior art low pressure pumping system.

In a "low pressure" pumping system, such as that schematized in, FIG. 1, a single pump P is used, whose inlet is connected to a mixing chamber MC. The tanks containing the solvents A, B, C are connected to this mixing chamber MC by means of solenoid valves EV1, EV2, EV3 for solvents A, B, C. An associated control set PC adjusts the opening of the solenoid valves one by one while observing predetermined ratios between their respective opening times as a function of the desired concentration ratios between the solvents injected. The passage of the eluates coming from column SC is detected by a detector ES.

Systems of this type have the advantage of working with a single pump, but they also present a drawback inherent in their method of operation. When each solenoid valve opens (EV2, EV3 for example), the solvent in the feed line coming from the tank is prevented by its inertia from following instantly the strong acceleration that is applied thereto by the suction of the pump. A cavitation generating bubbles occurs then. As a result, the mixing achieved loses its precision and the instantaneous flow rate is subject to variations according to the proportion of gas mixed with the liquid continually. These effects are amplified if solvents reacting with one another by producing gas are mixed together.

Figure 2:
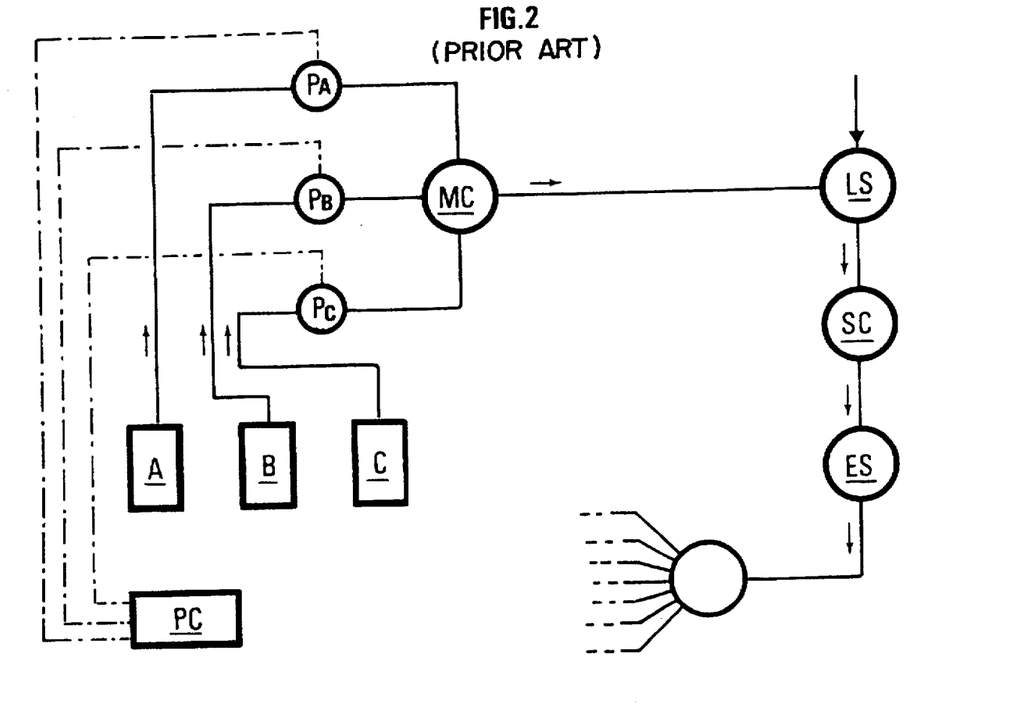
FIG. 2 shows an example of a system of a prior art high pressure pumping system.

In a "high pressure" pumping system, such as that schematized in, FIG. 2, one pump is used per solvent and the outlets of all the pumps PA, PB, PC are connected in parallel to a dynamic type mixing chamber MC. The mixing of the solvents is in keeping with the flow rates of each pump. Since mixing is achieved under a high pressure, the formation of bubbles is most often prevented and the proportions of each constituent are easily determined by controlling the flow rate of each pump. A notable drawback of this type of pump is its reduced dynamic working by comparison with that obtained with the "low pressure" system. In fact, the flow rate greatly depends on the outlet pressure and the flow dynamic rate is reduced in a ratio of 5 to 10, so that the gradients obtained lack precision.

The pumps used generally comprise one or several pistons that are moved alternately in pump barrels, by a motive means. The pistons can be in contact with rotary cams. The profile of the cams, their eccentricity and/or their driving speed are adjusted to vary the flow rate of the liquids pumped. The pistons can also be in contact with nuts by means of balls, the nuts being moved alternately by means of endless screws. One or several direct-current or stepping motors controlled by a microcalculator drive them into rotation.

EP Patents 40.161, 194,450 and 309,596 for example describe pumps for liquid chromatography applications, and embodiments in which a pump can be associated with a system of solenoid valves to obtain elution gradients with several solvents.

SUMMARY OF THE INVENTION

The pumping system according to the invention is of the modular type. It allows, through a combination of pumping unit modules, to obtain a great variety of easily modifiable configurations whose working characteristics can be changed at will without modifying the structure of their driving elements.

The pumping system according to the invention includes at least one pumping set that is achieved by combining in series reciprocating pumping units with each having a suction phase and a discharge phase. These units are phase-shifted in relation to one another. Each one includes a piston sliding tightly in a pump barrel and associated with adjustable reciprocating displacement means.

The pumping system according to the invention includes in each pumping set a number n,equal to or greater than 1, of primary pumping modules consisting each of at least one first pumping unit, these modules being connected respectively to n fluid tanks by n pipes provided each with unidirectional control means opening during the suction phase, a single secondary pumping unit and a collecting head connected in parallel to each of the n pipes by a nonreturn discharge valve, this collecting head being inserted between each primary module and the secondary unit, the reciprocating displacement means being suited for actuating the secondary unit so that it draws intermittently a fraction of the volume of fluid discharged in the collecting head by the corresponding primary pumping unit and it thereafter discharges the fraction with a substantially constant flow rate out of the collecting head.

According to an embodiment of the invention, primary pumping module also comprises a second pumping unit located upstream from the first primary pumping unit, the reciprocating displacement means of this second primary pumping unit being suited for giving a substantially constant flow rate during the suction.

The reciprocating displacement means of each first primary pumping unit is preferably suited for precompressing the fluid drawn thereby prior to the start of each of its discharge phases.

According to an embodiment, the reciprocating displacement means of each pumping unit comprises for example a nut or a threaded ring and a threaded rod, a motive means for translating the nut or the ring alternately in one direction and in the opposite direction with respect to the threaded rod, by driving the piston of the pumping unit, and a control set suited for controlling the displacements of the pumping units so that the total volume of fluid entering the collecting head at each discharge of the primary units is substantially double the volume drawn by the piston of the secondary unit.

The reciprocating displacement means of each pumping unit can also comprise adjustable-eccentricity cams driven into rotation by a motor, the eccentricities of the cams being so selected that the total volume of fluid entering the collecting head at each discharge of the primary units is substantially double the volume drawn by the piston of the secondary unit.

The control set comprises for example means for measuring the pressure in each pumping unit, means for detecting the position of each piston of the various pumping units and a microcalculator connected to the measuring means and to the detection means, that is programmed to move the different pistons so as to obtain a constant discharge rate suited to the number of primary modules opening into the collecting head.

The control set can include an interface module for the acquisition of measuring signals delivered by the measuring means and the detection means, and an interface module for controlling the motive means associated with the various pistons.

According to an embodiment of the invention, the pumping system comprises at least two primary pumping modules connected in parallel to the inlet of the collecting head, each one of them comprising at least one pumping unit, the control set being programmed to move the pistons of each of the primary pumping modules so as to obtain a determined proportion of each of the fluids in the fluid mixture of constant flow rate expelled out of the collecting head.

The control set can also be programmed to proportion the volume of fluid drawn at a constant flow rate by the second primary module of each primary pumping module.

According to an embodiment, the motive means of each pumping unit comprises an electric motor controlled by the microcalculator by means of an interface module, a nut integral with the rotor of the motor, and a threaded rod resting against the piston of this unit by means of a ball thrust.

Each pumping unit can comprise two pistons working in opposition and means for driving them together or separately so as to increase the reliability of the pumping system.

The system according to the invention allows a very great stability of the discharge rate and, in some cases to be obtained, of the suction rate, as well as of the mixing with a precise proportioning of the fluids coming in parallel from several tanks. It is easy to implement since the displacement patterns of the various pistons can be controlled with precision by means of a software.

For the same reason, modifications in the working conditions, required by a change in the series or series/parallel configuration of the pumping modules of the pumping system, can be easily achieved.

Precise control of the translation motions of the pistons also allows the transient effects due to too strong accelerations in the suction phase to be avoided, and therefore the formation of gas bubbles to be prevented.

Since the fluids are mixed at a high pressure in the collecting head, the appearance of bubbles resulting from a physico-chemical reaction with one another is prevented.

BRIEF DESCRIPTION OF THE DRAWINGS

Other features and advantages of the pumping system according to the invention will be clear from reading the description hereafter of embodiments given by way of non limitative examples, with reference to the accompanying drawings in which:

FIG. 8 shows a second implementation of the pumping system similar to that of FIG. 7, where cams are used to move the pistons, FIGS. 9A, 9B diagrammatically show, in connection with FIG. 5, how the respective displacement amplitudes f(x), g(x) of the primary and of the secondary pistons vary during a pumping cycle with a single primary pumping module, FIGS. 10A, 10B, 10C diagrammatically show, in connection with FIG. 6, how the respective displacement amplitudes f(x), g(x), h(x) of the primary and of the secondary pistons vary in the embodiment of FIG. 6 with two primary units in series, FIGS. 11A, 11B diagrammatically show, in connection with FIG. 7, how the respective displacement amplitudes f(x), g(x) of the pistons of the various parallel primary modules and of the secondary module vary during a pumping cycle, FIG. 12 diagrammatically shows the system according to the invention with its control set suited to an implementation mode.

DESCRIPTION OF THE PREFERRED EMBODIMENTS

The pumping system according to the invention is made up of pumping modules.

Each pumping module comprises (FIGS.3, 4) a pump barrel 1 provided with a cylindrical inner cavity 2. A rod 3 is partly fitted in the inner cavity 2 through an opening at the bottom of the barrel. A seal 4 is arranged around the rod to the inner cavity. Rod 3 is provided with a head 5. A spring 6 is placed between the head and the end of the barrel, so as to exert a permanent extraction force on the piston.

Figure 3:
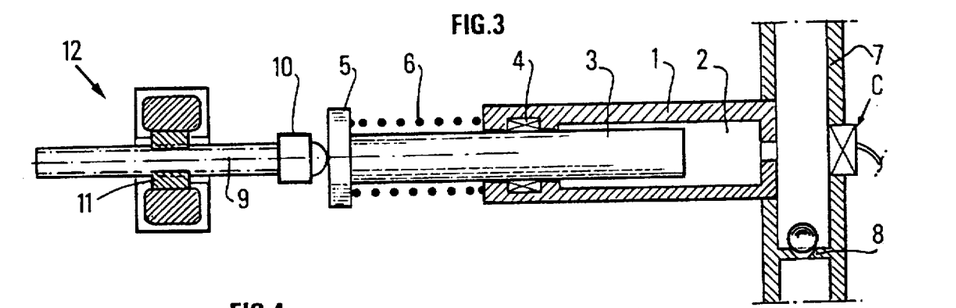
FIG. 3 shows a reciprocating-piston pumping element driven by the rotation of a ball screw.
Figure 4:
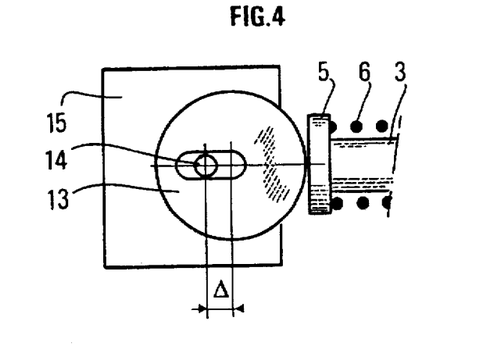
FIG. 4 shows a similar pumping element driven by the rotation of a cam.

At the opposite end, the inner cavity 2 communicates with a pipe 7 provided with a unidirectional valve 8 opening during the suction phase during which the rod 3 moves back, such as a ball check valve for example. A pressure detector C is placed for example in pipe 7 downstream from valve 8.

According to a first embodiment (FIG.3), the varying insertion of rod 3 in the inner cavity 2 is provided by the translation motion of an endless screw 9 resting against head 5 by means of a ball thrust 10. The means for translating the screw include for example a nut 11 fitted to screw 9, that is for example seated in the hollow rotor of a stationary electric motor 12 and driven into rotation thereby. The direction of translation of the screw is changed by inverting the direction of rotation of the motor at each pumping half cycle.

According to a second embodiment (FIG.4), the varying insertion of rod 3 in the inner cavity 2 is provided by the rotation of a cam 13 resting against head 5, whose shaft 14 is driven into rotation by a motor 15. The varying insertion of the rod in the cylindrical cavity 2 is obtained by changing the eccentricity d of the cam on its shaft.

The pumping system according to the invention comprises at least one pumping unit consisting of the series interconnection of a primary pumping module made up of at least one primary pump P (FIG. 5) or two primary pumps in series (FIG.6), with a secondary pump S that is phase-shifted with respect to the primary pump. The primary module communicates with a tank R containing a fluid to be pumped such as a solvent by a pipe T on which is interposed a unidirectional nonreturn valve V1. A second nonreturn valve V2 (FIG. 5) allowing access of the fluid in a collecting head CH is interposed on the same pipe downstream from the primary module. During its discharge phase, the secondary module S drives the fluid drawn into the collecting head CH towards a chromatographic column (not shown), for example through a pipe TS.

Figure 5:
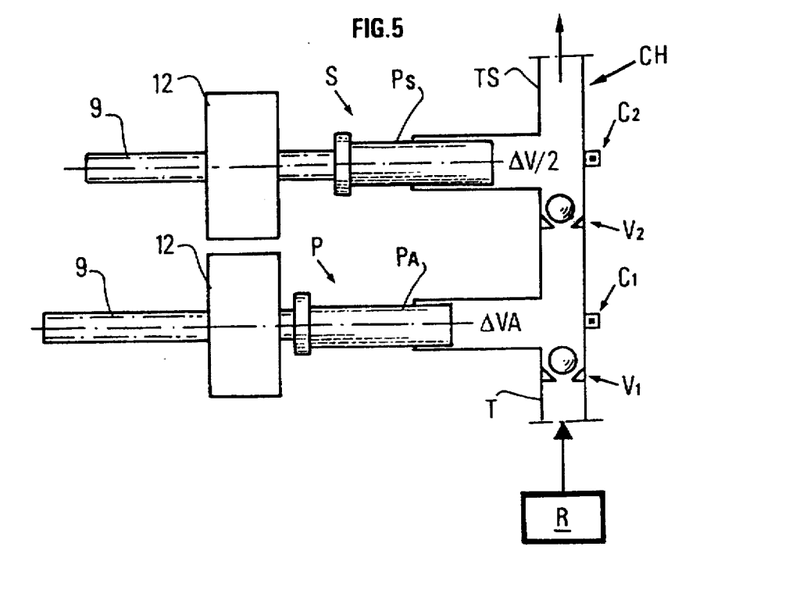
FIG. 5 shows a first embodiment of the pumping system according to the invention using ball screws to move the pistons, with a mixing head having a single inlet.

During the discharge phase of the piston PA of the primary pump P (phase j ranging from 0 to $\Pi$), when a volume $\Delta VA$ is driven thereby towards the collecting head CH according to a forward motion function f(x), the retreat of the piston PS of the secondary module is ordered so that it draws a volume $\Delta VS=\Delta VA/2$, according to a back motion function g(x), by taking it from the volume discharged by the primary module. The volume expelled towards pipe CH is thus equal to $\Delta VA/2$. When the piston PA of the same primary module passes into the suction phase (phase j ranges from $\Pi$ to $2\Pi$) with the closing of valve V2, the piston PS of the secondary module passes into the discharge phase and expels the volume $\Delta VS=\Delta VA/2$ drawn previously towards pipe TS.

Figure 9A:
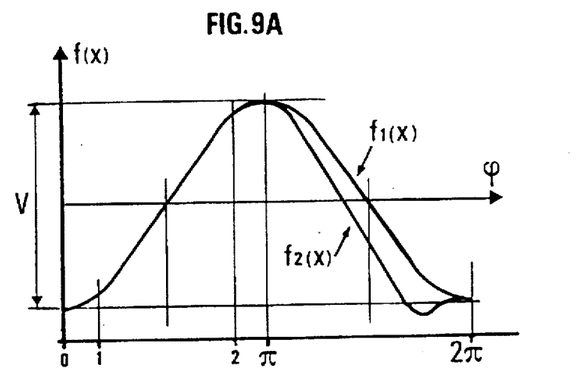
Figure 9B:
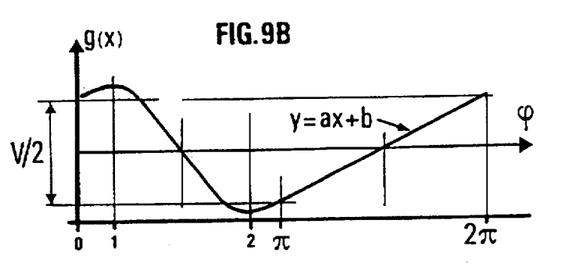

The flow expelled through pipe TS is thus constant provided that the motion functions f(x) and g(x) are so selected that the sum of their derivatives f'(x)+g'(x) is permanently constant. During the discharge phase of the secondary pump S, between $\Pi$ and $2\Pi$(FIGS.9A, 9B), a linear motion of the form y=a.x+b whose slope is a =f'(x)+ g'(x) is imposed on the piston PS thereof, so as to impose a constant flow rate. The velocity f'(x) of the primary piston PA is considered to be zero here although it is in a back motion phase, because the effect it would have on the fluid in pipe CH is inhibited by the closing of valve V2.

The observance of this condition gives a constant flow rate only with liquids at relatively low pressures, where the compressibility thereof can be disregarded. In the opposite case, one must take into account that, in the suction phase, the pressure in the chamber of the primary pump is substantially that of the atmospheric pressure. Before the discharge can start, the pressure in the primary chamber must be raised to the pressure of the secondary module. It is therefore preferable to follow the suction curve f2(x) (FIG.9A) so as to have time to reach the discharge pressure required when j=$2\Pi$.

Figure 6:
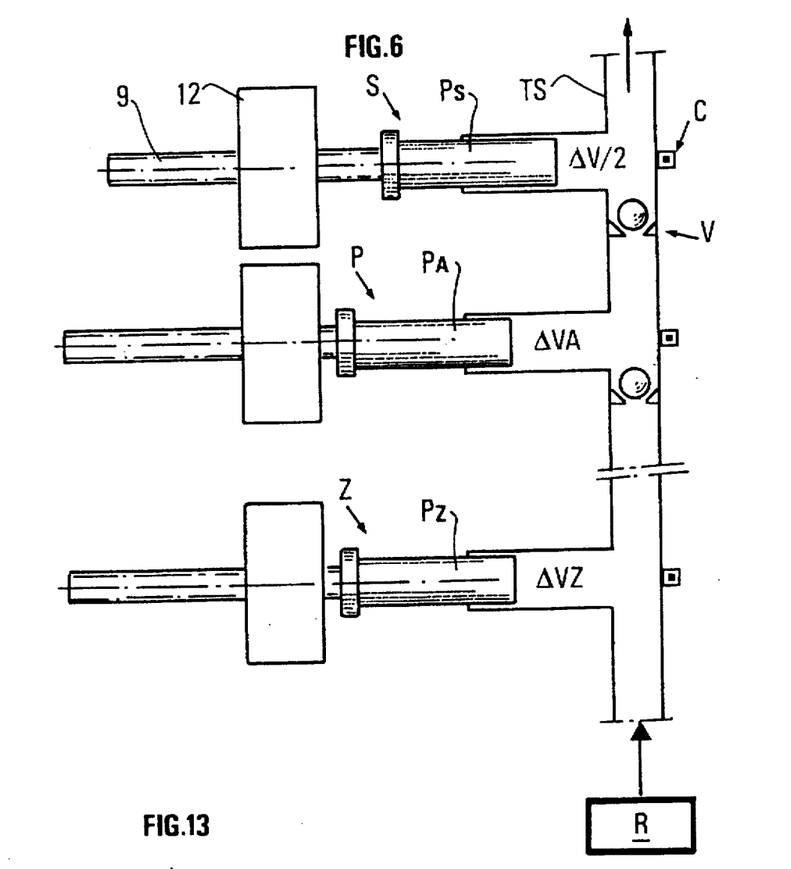
FIG. 6 shows another embodiment of the invention with pumping module comprising two primary pumping modules in series, FIG. 7 diagrammatically shows an implementation of the system according to the invention comprising several primary pumping units in parallel on a single mixing head.
Figure 10A:
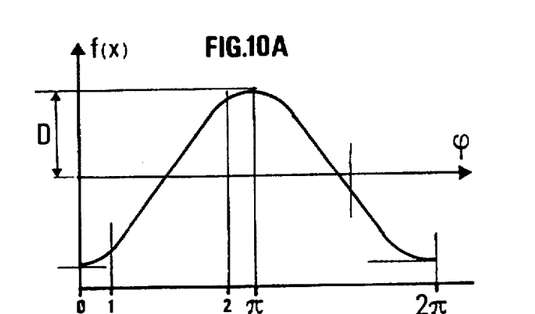
Figure 10B:
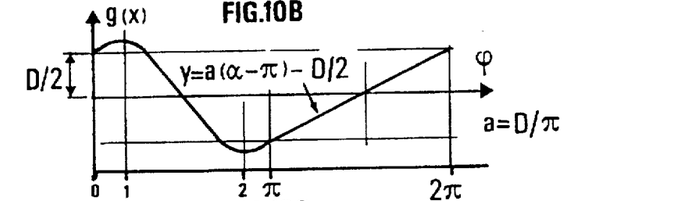
Figure 10C:
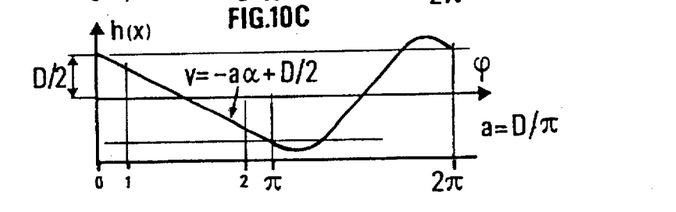

According to the embodiment of FIG. 6, the pumping system comprises two primary pumps P and Z in series on the same pipe connected to a tank R. The displacement diagrams of the primary pump P and of the secondary pump S (FIGS.10A, 10B) are identical to those of the corresponding units of the embodiment of FIG.5. The upstream primary unit Z is here so controlled that its piston moves linearly between 0 and $\Pi$, from V/2 to $-$V/2, and follows the same variation law (FIG.10C) as the secondary unit S between $\Pi$ and $2\Pi$.

A distinctive feature of this embodiment is that its flow rate is also constant during the suction phase. It is particularly well-suited for simulated moving bed chromatography operations or when the suction tubes are long enough for the suction to produce cavitations generating gas bubbles.

In order to even better prevent cavitation phenomena during suction, the motion function f(x) of the primary piston PA is so selected that its acceleration f''(x) is constant.

Figure 7:
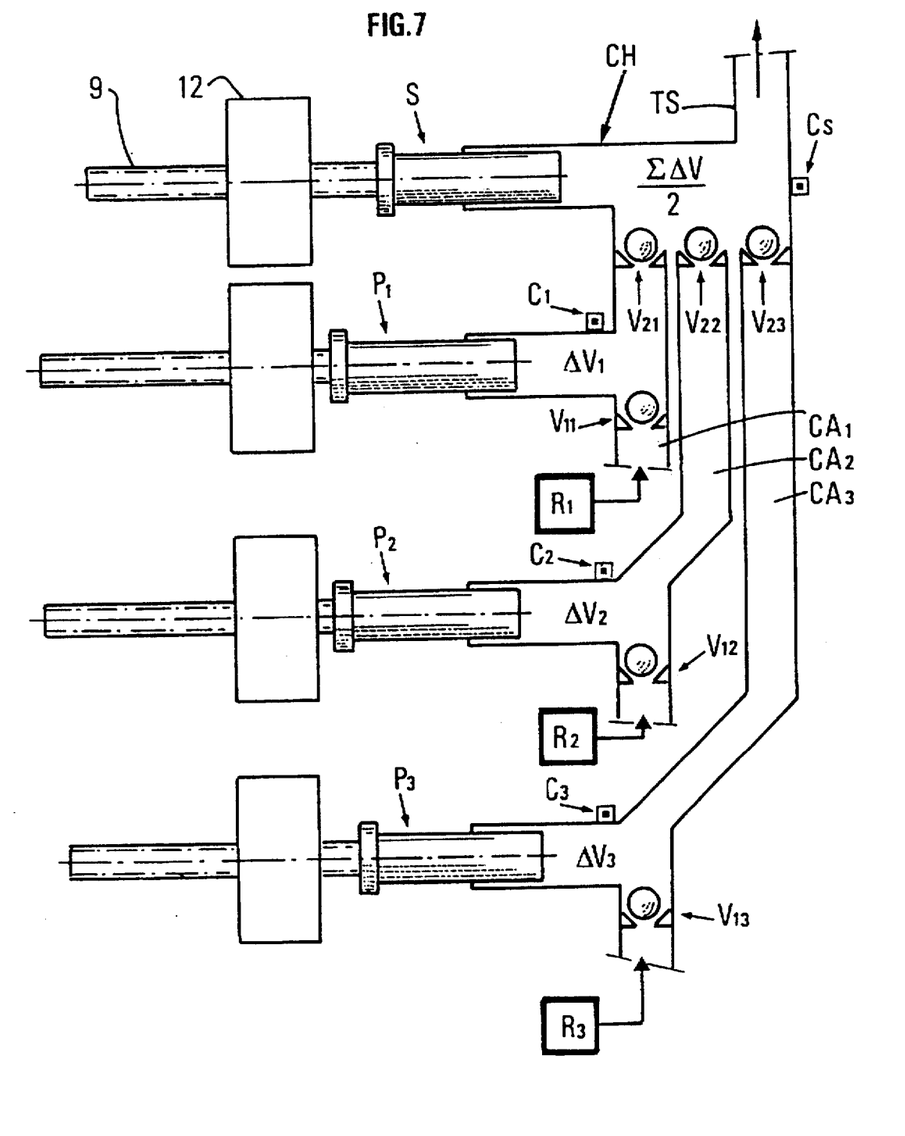

According to the embodiment of FIG. 7, an elution gradient is achieved by using a collecting head CH with several inlets. In the example shown, the system includes three primary pumping modules P1, P2, P3 communicating respectively through pipes with three tanks R1, R2, R3 containing three fluids to be mixed through pipes CA1 to CA3 provided with nonreturn suction valves V11–V13. Pipes CA1, CA2, CA3 open into the collecting head CH by means of nonreturn valves V21–V23. The system includes a single secondary module S freely communicating with the collecting head CH.

Whatever their number may be, the primary modules P work in phase with one another. The respective proportion of the fluids discharged in the collecting head CH can be adjusted by varying the stroke of each one of the pistons of the primary units P1 to P3, provided that, as previously:

the sum of the three volumes $\Delta V(P1)$, $\Delta V(P2)$ and $\Delta V(P3)$ of the three primary chambers remains double the volume $\Delta V(S)$ drawn and discharged by the secondary module S, so that the flow rate of the pumping system remains substantially constant, and the sum of the derivatives f1(x), f2(x) and f3(x) and g'(x) of the motion functions remains permanently constant, with the same convention according to which the velocity f'(x) of the primary piston P is considered to be zero in its back motion phase.

More generally, if n (n>1) is the number of primary modules and a represents a constant, the variation stroke of the primary pistons is so adjusted that $$\sum_n \Delta V(P_n) = \Delta V(S) \quad (1)$$

and one makes sure that the following equality is permanently maintained:

$$g'(t) + \sum_n f_n(t) = a \quad (2)$$

where fn(t) is the displacement velocity of the piston of the primary pump Pn.

Under such conditions, the secondary pumping unit always acts upon the same volumes of fluid by keeping the expelled flow constant, whatever the possible changes in the constituent proportions that may have been ordered at the level of the primary stages P.

In the embodiment of FIG. 7, these conditions are achieved by imposing continually an appropriate direction and speed of rotation on the various driving motors.

Figure 8:
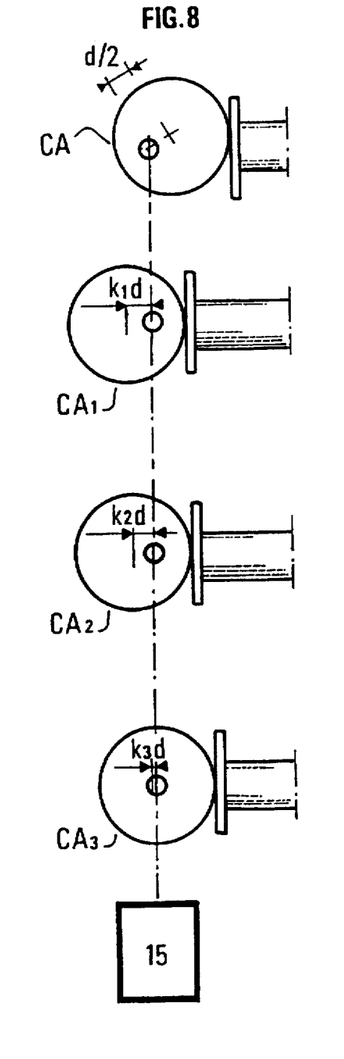

In the embodiment of FIG. 8, the cams CA1–CA3, CAs associated with the various pistons can be driven into rotation by the same motor 15. However, in order to obtain a more precise control of the reciprocating motion to be communicated to each piston, it is preferable to associate a different motor with each cam.

The eccentricity of cams CA1–CA3 is adjusted as a function of the respective rates of the various fluids to be mixed and in such a way that the sum of the eccentricities of the various primary pumps P1, P2, P3 for example is equal to the eccentricity d that the cam would have if a single primary module was used. In the example shown, the three constituents are mixed respectively with the rates 0.5. d, 0.35. d and 0.15. d by the adjustement of the cams CA1–CA3.

An embodiment of the cams driving the primary pistons, which allows a constant acceleration to be obtained while avoiding cavitations, consists for example in selecting a cam profile consisting of arcs of a parabola.

Figure 12:
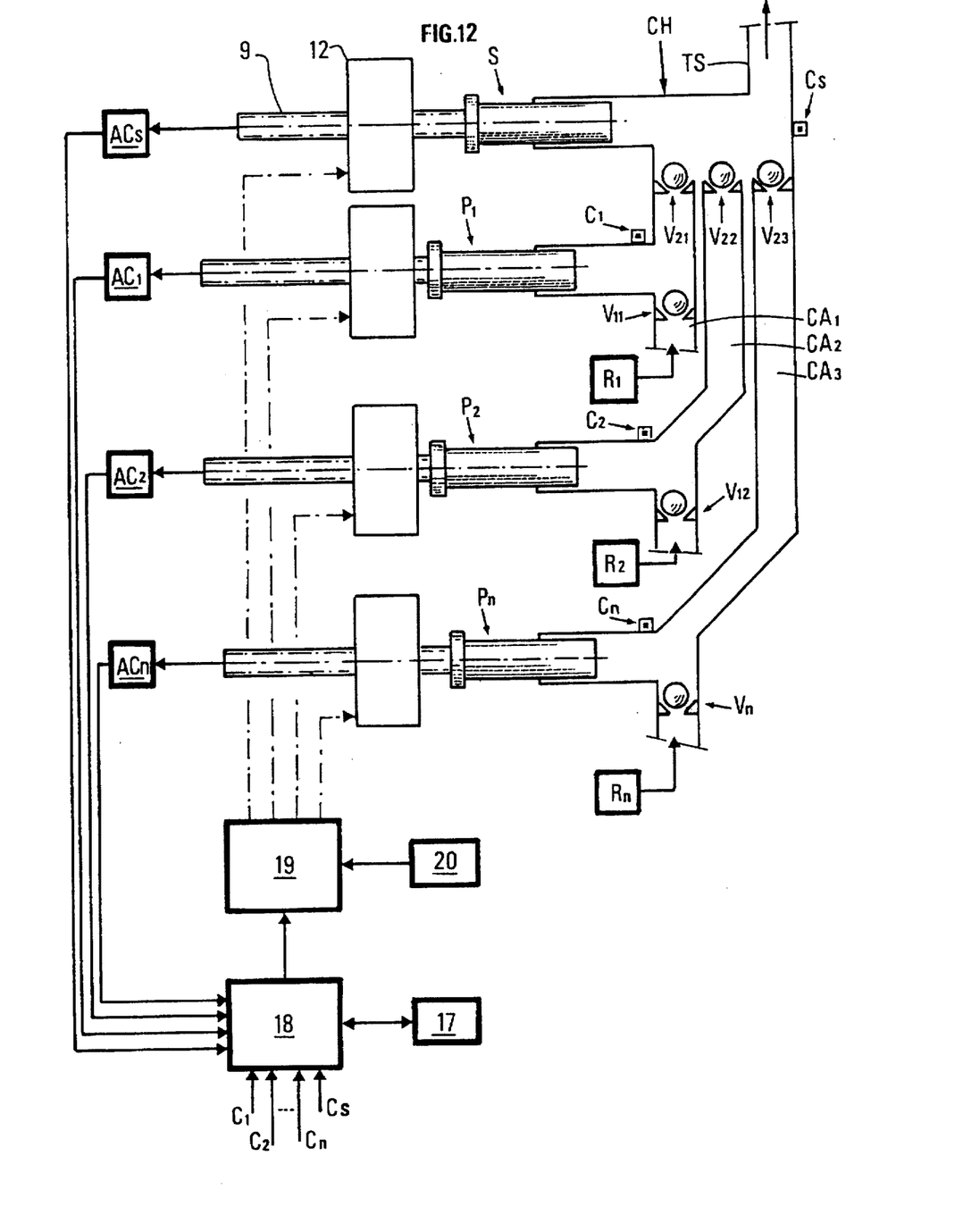

The pumping system (FIG. 12) is controlled by a control set comprising a microcalculator 17 provided with an interface card 18. Angle encoders AC1, AC2, ACn and ACs are associated respectively with each of the n (n≧1) primary modules P1 to Pn and with the secondary module S. The signals coming from these angle encoders, which are representative of either the angle of rotation of each screw and of its direction (FIG. 12), or of the angle and of the direction of rotation of each cam in the embodiment of FIGS.4 to 8, are acquired by the interface card 18 associated with microcalculator 17. The pressure detectors C1, C2 ... Cn and Cs for measuring the pressures in each of the modules are also connected to this card 18. The electric motors (low-inertia direct-current motors or stepping motors) used for driving the pistons are supplied by a power interface 19, itself connected to an electric generator 20.

Figure 11A:
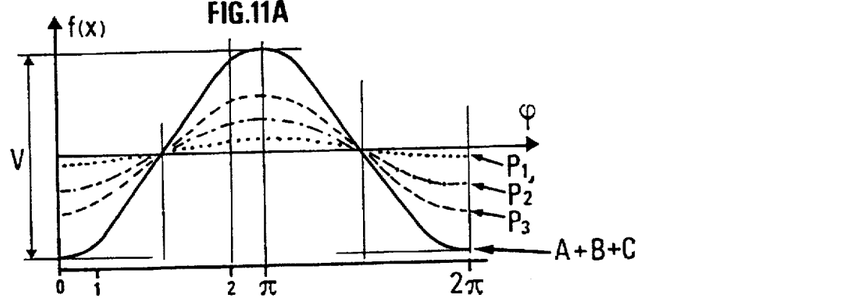
Figure 11B:
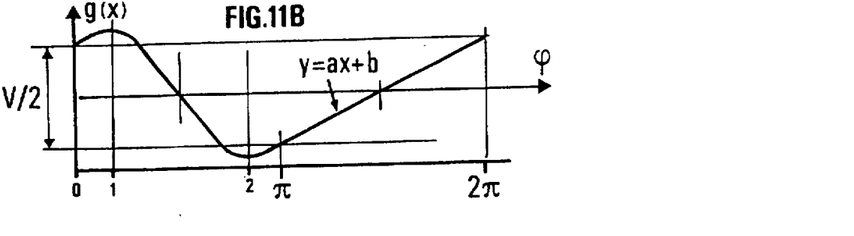
Figure 14A:
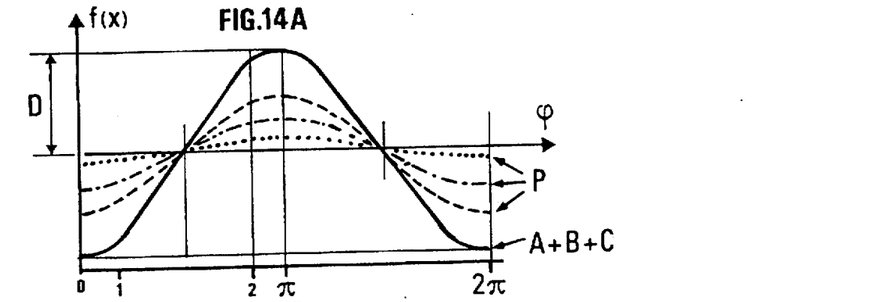
FIGS. 14A, 14B, 14c show the corresponding diagrams obtained by controlling the primary and the secondary pistons.
Figure 14B:
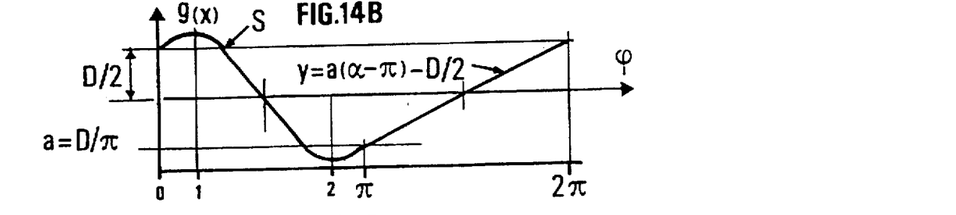
Figure 14C:
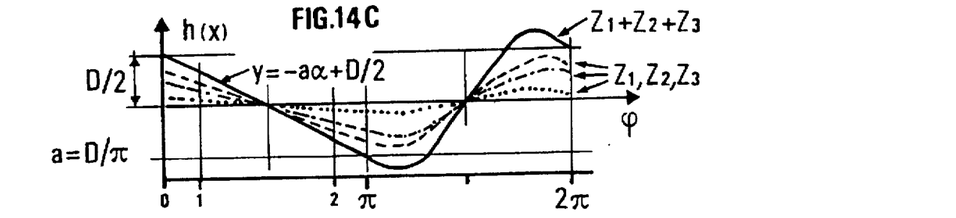

Microcalculator 17 is programmed to elaborate the control signals defining the direction of rotation and the speed of rotation of each motor 12, from data supplied by the angle encoders AC and the pressure detectors C, so as to continually achieve a constant flow rate, while avoiding possible cavitation effects, in accordance with the relations 1 and 2 and the displacement curves of FIGS.9, 11, 14 for example.

In the case where the rate of each constituent has to be modified, the displacement laws of the various primary pistons can be changed by a simple modification of the control software. The composition of the mixture delivered can thus be modified at will without changing its flow rate or its regularity.

The previous pumping units P, S and Z lend themselves to various combinations.

The base pumping system comprises, as stated above, at least one primary module (a primary unit P or two primary pumps P and Z in series) associated with a collecting head CH and a secondary pump S (FIGS.5, 6). This base combination can be easily modified by connecting several primary modules in parallel onto the same collecting head CH.

Figure 13:
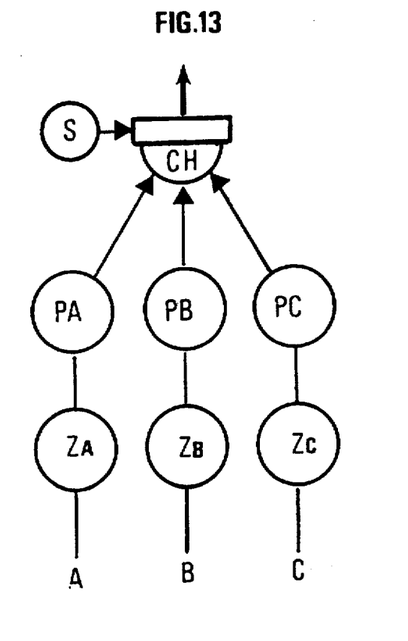
FIG. 13 shows a mode of series and/or parallel interconnection of pumping units.

It may for example be seen that, according to the embodiment of FIG. 13 for example, it is possible to connect to a single mixing head CH several primary branches comprising each two primary pumping units P and Z in series. The modules PA, PB, PC and module S work (FIGS.14A, 14B) in a way that is similar to those described in connection with FIGS.7, 8. Modules ZA, ZB and ZC are controlled so as to follow the displacement diagrams of FIG.14C. Their respective elongations are proportional to the elongation of the single module Z of FIG.6, with proportionality coefficients depending on the wanted elution gradient.

Without departing from the scope of the invention, each single-piston pumping unit can be replaced by a unit with two pistons arranged in opposition and connected to each driving means (screw/nut or cam) by pneumatic means, each of the connections being controlled by a solenoid valve. One piston is enough for driving the pumping unit. For maintenance operations or in case of a breakdown, one of the pistons can be dealt with by switching the solenoid valves.

We claim:

1. A pumping system comprising a fluid reciprocating primary pump and a reciprocating secondary pump, the pumps including reciprocating displacement pistons sliding in pump barrels, under action of a reciprocating displacement device with each piston having a suction phase and a discharge phase, the secondary pump being operated with phase shifts with respect to the primary pump to intermittently draw a fraction of the fluid discharged thereby, and to discharge thereafter the fraction at a substantially constant rate into an outlet pipe, a common collecting head, the primary pump having n(n>1) primary pumping modules each including at least one primary pumping unit, the modules being connected respectively to n fluid tanks by first unidirectional valves and discharging into the common collecting head fluids drawn by means of second unidirectional valves, and the secondary pump having at least one secondary unit for intermittently drawing, into the common collecting head, a fraction of fluids coming from the primary pumping wherein:

(a) a sum of volumes scavenged by the pistons of the n primary pumping modules remains constantly equal to a volume scavenged by the secondary pumping unit; and (b) the reciprocating displacement device for moving the piston of the secondary pump applies permanently thereto a displacement function g(t) such that a sum of displacement rates of the pistons of the n primary pumping modules and a velocity of a piston of the secondary pumping unit is constant at least during a time interval of opening of the second unidirectional valves.

2. A pumping system as claimed in claim 1, wherein each primary pumping module comprises a first and a second primary pumping unit arranged in series and each second primary pumping unit is associated with the reciprocating displacement device to provide a substantially constant flow rate thereto during the suction phase.

3. A pumping system as claimed in claim 1 wherein the reciprocating displacement device associated with each first primary pumping unit precompresses fluid drawn thereby prior to a start of each discharge phase.

4. A pumping system as claimed in claim 1, wherein the reciprocating displacement device associated with each pumping device comprises one of a nut or a threaded ring and a threaded rod for translating the nut or the ring alternately in one direction and in an opposite direction in relation to the threaded rod, by driving a piston, and a control set controlling displacement of the piston of each secondary pumping unit in order to meet conditions (a) and (b).

5. A pumping system as claimed in claim 1, wherein the reciprocating displacement device associated with each pumping unit comprises a cam having an adjustable eccentricity that is driven into rotation by a motor with eccentricity of each cam being selected to obtain a determined proportion of each of a plurality of fluids in the mixture of fluids discharged in the common collecting head, and a control set for controlling rotation of the cam driving pistons of the primary pumping units in order to meet conditions (a) and (b).

6. A pumping system as claimed in claim 5, wherein the control set controls displacement of the pistons so that a total volume of the plurality of fluids coming from the primary pump is substantially double the volume drawn by a piston of the secondary unit.

7. A pumping system as claimed in claim 5, wherein the control set comprises means for measuring pressure in each pumping unit, means for detecting a position of each piston of the pumping units and a microcalculator, connected to the measuring means and to the detection means, and programmed for moving the pistons to produce a constant discharge rate suited to a number of the primary pumping modules.

8. A pumping system as claimed in claim 7, wherein the control set comprises an interface module for acquisition of measuring signals delivered by the measuring means and the detection means, and an interface module for the control of the means for translating pistons.

9. A pumping system as claimed in claim 1, comprising:
a plurality of primary pumping modules connected in parallel to an inlet of the collecting head, each primary pumping module comprising at least one pumping unit, a control programmed to move the pistons of each of the primary pumping modules to obtain a determined proportion of each fluid in the fluid mixture of constant flow rate delivered by the pumping system.

10. A pumping system as claimed in claim 9, wherein the control is programmed to proportion a volume of fluid drawn at constant flow rate by the secondary primary module of each primary pumping module.

11. A pumping system as claimed in claim 1, wherein each pumping unit comprises two opposing pistons and means for driving the opposing pistons selectively.

12. A pumping system as claimed in claim 1, wherein the reciprocating displacement device for moving the pistons provides an acceleration applied to the pistons which is constant during suction phases.

* * * * *